United States Patent [19]
Trigger

[11] Patent Number: 5,950,830
[45] Date of Patent: *Sep. 14, 1999

[54] PACKAGING FOR PATCHES

[75] Inventor: David Trigger, Champniers-Reilhac, France

[73] Assignee: Ethical Pharmaceuticals (U.K.) Limited, Ely, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/849,892

[22] PCT Filed: Dec. 20, 1995

[86] PCT No.: PCT/GB95/02976

§ 371 Date: Aug. 22, 1997

§ 102(e) Date: Aug. 22, 1997

[87] PCT Pub. No.: WO96/19394

PCT Pub. Date: Jun. 27, 1996

[30] Foreign Application Priority Data

Dec. 21, 1994 [GB] United Kingdom ................ 9425783

[51] Int. Cl.⁶ ............................. A61B 17/06; A61F 13/02
[52] U.S. Cl. .......................................... 206/440; 424/449
[58] Field of Search .................... 206/438, 440, 206/461, 467, 471; 424/449; 53/478, 467, 471

[56] References Cited

U.S. PATENT DOCUMENTS

| | | |
|---|---|---|
| D. 304,685 | 11/1989 | Hadtke . |
| D. 342,446 | 12/1993 | Parker et al. . |
| D. 363,217 | 10/1995 | Flynn . |
| 3,174,621 | 3/1965 | Watson . |
| 3,255,880 | 6/1966 | Grossman . |
| 4,788,062 | 11/1988 | Gale et al. ............................. 424/449 |
| 4,844,251 | 7/1989 | Gueret ................................... 206/440 |
| 4,915,102 | 4/1990 | Kwiatek et al. ...................... 206/440 |
| 5,044,495 | 9/1991 | Wyslotsky ............................. 206/461 |
| 5,115,913 | 5/1992 | Anhauser et al. .................... 206/440 |
| 5,209,354 | 5/1993 | Thornhill et al. . |
| 5,292,003 | 3/1994 | Baghdassarian . |
| 5,325,961 | 7/1994 | Ford et al. . |
| 5,413,567 | 5/1995 | Barth et al. ............................ 206/440 |
| 5,422,119 | 6/1995 | Casper .................................. 424/449 |
| 5,423,737 | 6/1995 | Cartmell et al. ...................... 206/440 |
| 5,439,100 | 8/1995 | Gordon et al. ........................ 206/461 |
| 5,505,306 | 4/1996 | Akemi et al. ......................... 206/440 |
| 5,716,636 | 2/1998 | Horstmann et al. .................. 424/449 |

FOREIGN PATENT DOCUMENTS

| | | |
|---|---|---|
| 0 211 312 | 2/1987 | European Pat. Off. . |
| 0 635 262 | 1/1995 | European Pat. Off. . |
| 25 15 016 | 11/1975 | Germany . |
| 4-51782 | 10/1989 | Japan . |
| 234280 | 11/1992 | New Zealand . |
| 1310923 | 3/1973 | United Kingdom . |
| 90/13494 | 11/1990 | WIPO . |
| 95/00122 | 1/1995 | WIPO . |

*Primary Examiner*—David T. Fidei
*Assistant Examiner*—Luan K. Bui
*Attorney, Agent, or Firm*—Flehr, Hohbach, Test, Albritton & Herbert LLP

[57] ABSTRACT

A package (12, 14) contains a transdermal patch (1) releasably mounted on a release liner (3) larger than the patch so that a peripheral edge (1a, 1b) of the patch is spaced from the edge of the release liner (3) by a border (7). The package (12, 14) is shaped and being sufficiently rigid that said edge of the patch is maintained spaced from the package. The package comprises a container (12) and a closure (14). The container has a recess containing the patch (1) and the release liner (3), and the recess has a base (18, 22) which includes a raised portion (18) located in the base so that, with the patch (1) facing the base, the edge (1a, 1b) of the patch is maintained spaced from the base in any position of the release liner within the recess.

8 Claims, 3 Drawing Sheets

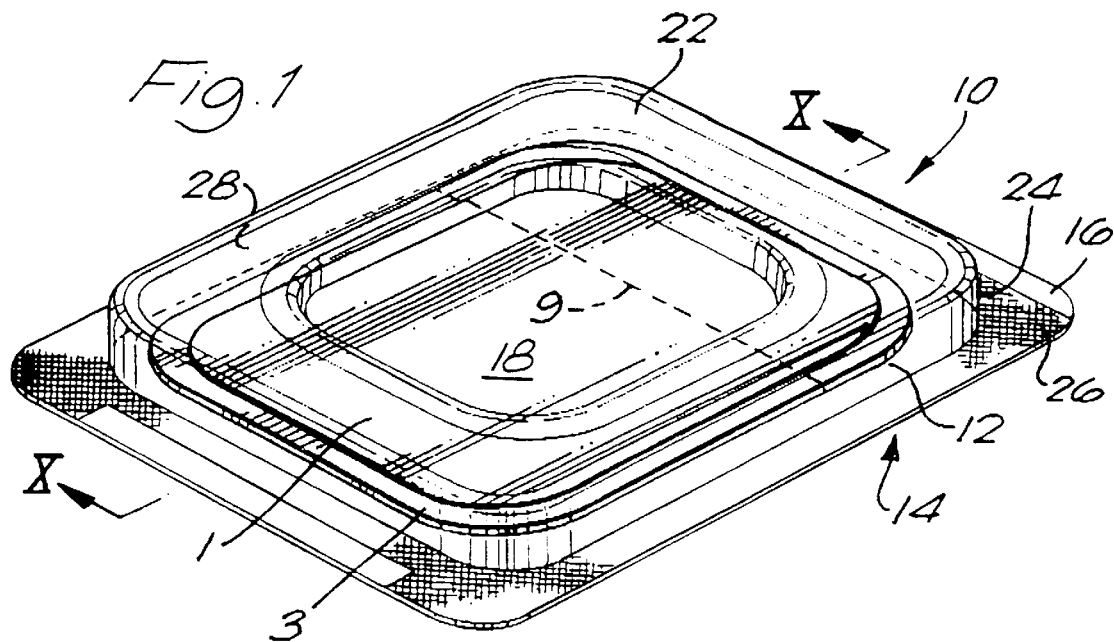
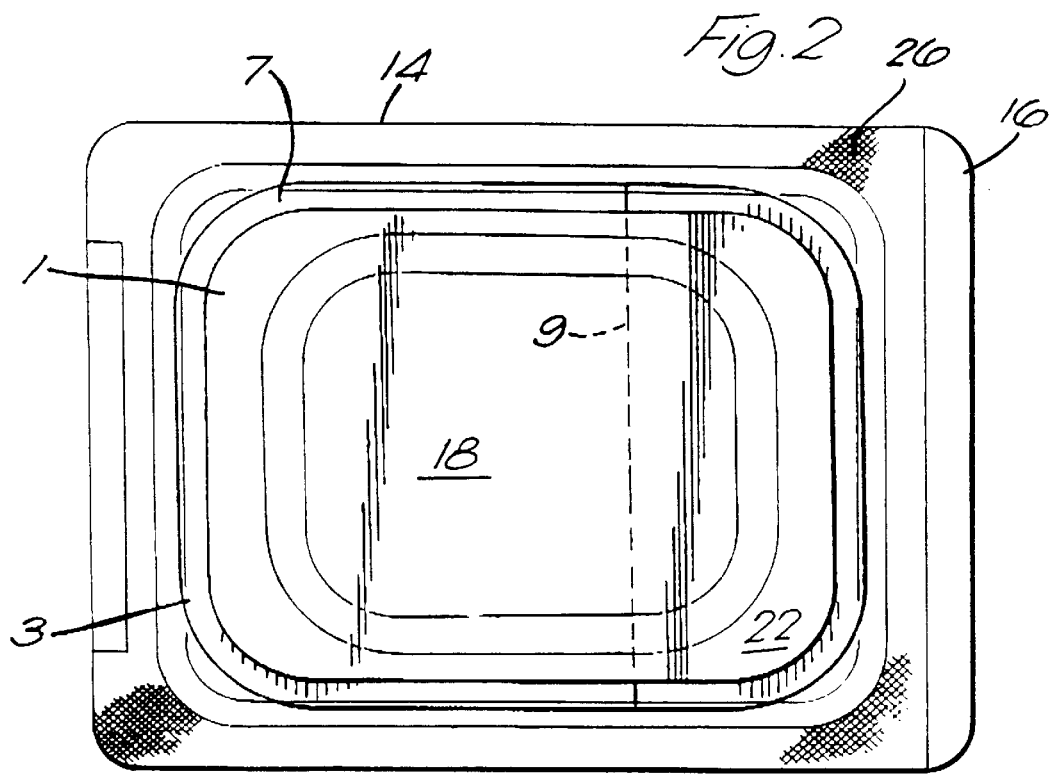

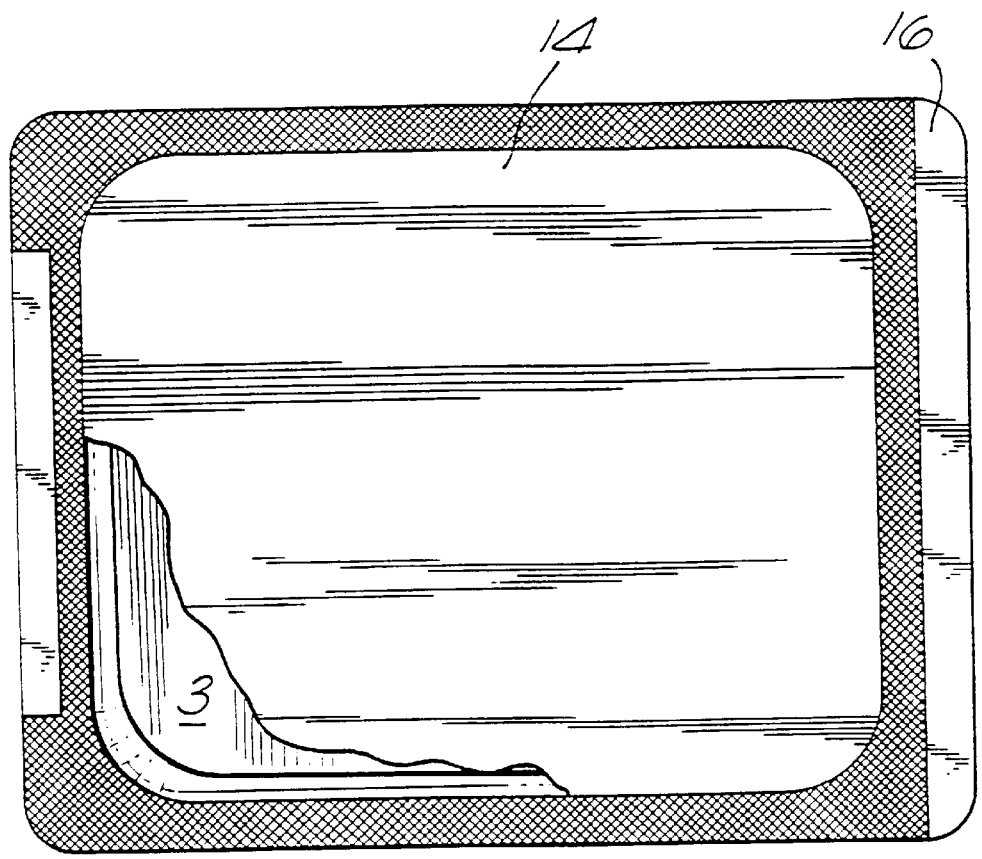

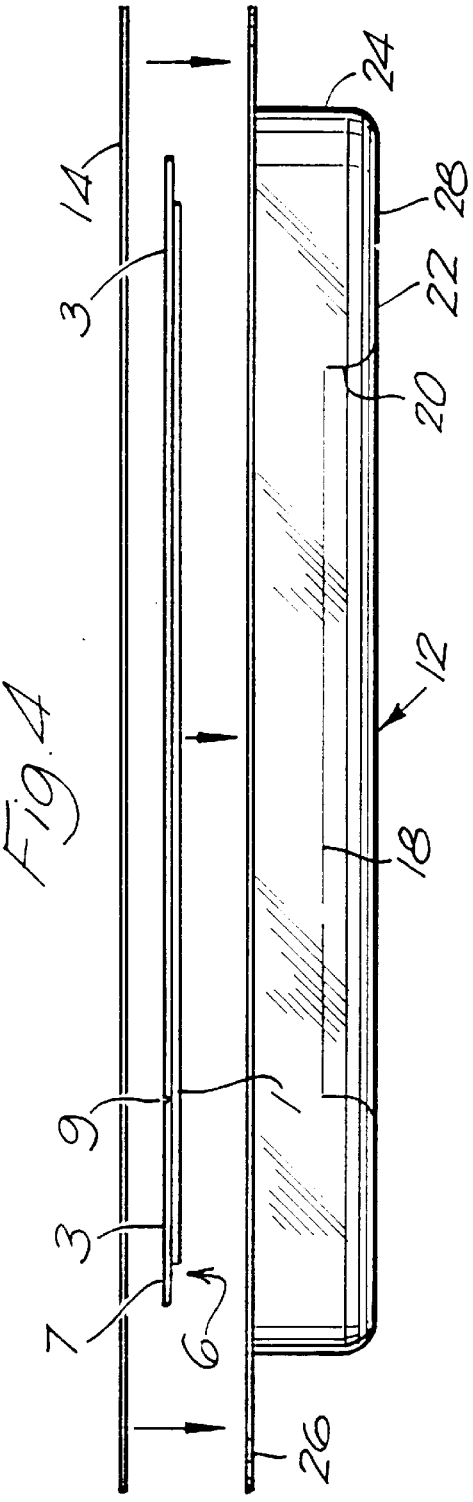
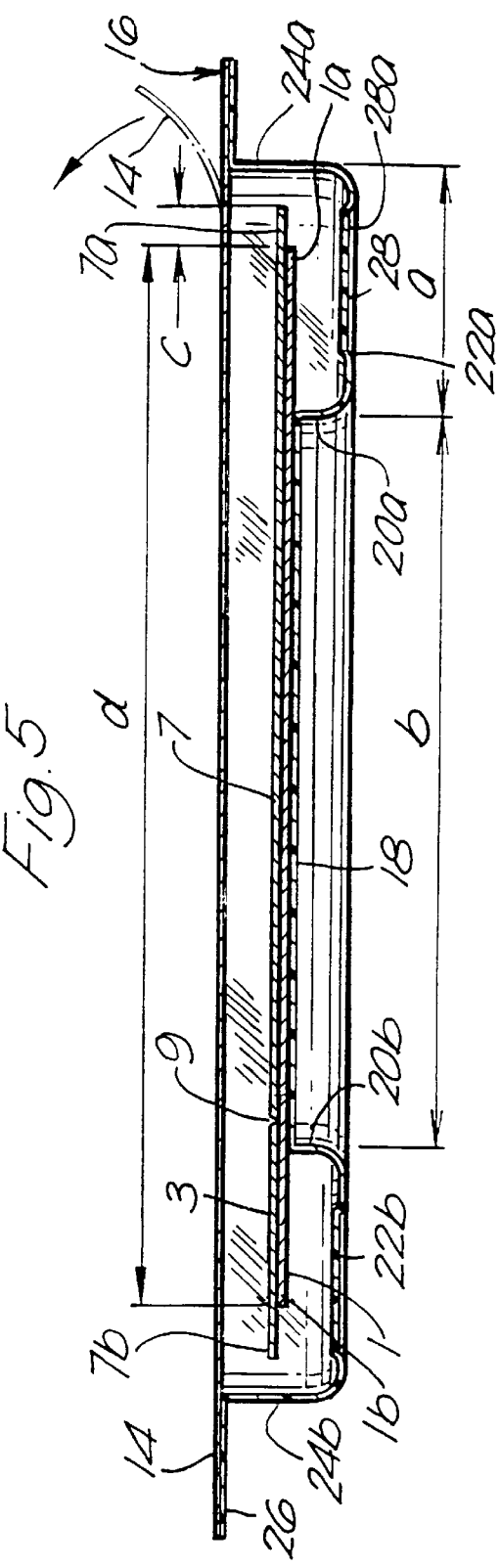

PACKAGING FOR PATCHES

TECHNICAL FIELD

The present invention relates to a package containing a patch for application to the skin, particularly but not exclusively a transdermal patch. The present invention also relates to a kit for making such a package and to the use of such a package.

BACKGROUND OF THE INVENTION

Medical transdermal patches have many uses, for example in hormone replacement, anti-anginal, travel sickness and smoking cessation therapy. Although various types of transdermal patches have been used, it is now generally preferred to use a patch which has a backing sheet and one or more layers, including an adhesive layer which attaches the patch to the skin. The adhesive layer is typically a viscous liquid containing at least one active component. The patch is supplied on a release-liner covering the adhesive, which is peeled off immediately before applying the patch to the skin. The active component then passes through the skin.

It is known to package such patches in a polymer or multi-layer laminate envelope or sachet. WO 95/00122 (published Jan. 5, 1995, after the priority date now claimed), shows an example of this, in which a release liner carrying four patches is enclosed in a resealable bag made of plastic film or foil laminate. A modified package is known from Japanese Utility Model publication 1-155428 (accepted publication no. 4-51782) in which the patch is mounted on a release liner provided with raised dimples to minimise contact between the envelope or sachet and the patch. A similar package has been marketed, for example, by Ortho-Cilag under the name Evorel™. It has been found that although the raised dimples provide a limited degree of protection, they do not prevent pressure on the patch due to handling, leading to oozing of the viscous adhesive which forms a sticky ring around the patch. This results in a tendency for the patch to stick to the envelope or sachet.

It is also known to provide a blister-pack in which a patch attached to a release liner, which is the same size as the patch itself, is located in a shallow blister formed between a plastic moulding and a foil lidding. A rib is formed around the blister, to increase rigidity of the otherwise fragile pack which is susceptible to curling. Such a patch is believed to have been marketed under the name TRIALSAT™ by Beta Pharmaceuticals.

Use of a release liner which is the same size as the patch means that the only sticky part of the patch is at the periphery, though adhesive can ooze around the edges of the patch. However, because the patch and release liner are the same size, it can be difficult and messy to separate the two. It may be undesirable that the active component is touched by a user, except at the intended application point. Furthermore, the need for a reinforcing rib around the blister increases the overall size of the package, so that the package occupies a much larger volume than the patch itself.

SUMMARY OF THE INVENTION

The present invention seeks to overcome the above problems, by providing a novel package for a patch in which the patch is substantially prevented from sticking to the package. In addition the release liner can be more readily separable from the patch and the package may be rigid enough to provide a degree of mechanical protection for the patch without the overall size of the package necessarily becoming excessive in comparison to the size of the patch.

Accordingly, the present invention provides a package containing a patch for application to the skin having an adhesive layer by which the patch is releasably mounted on a release liner larger than the patch, the peripheral edge of the patch being spaced from the peripheral edge of the release liner by a border region of the release liner, the package being sufficiently rigid and being shaped so that said peripheral edge of the patch is substantially prevented from contacting any part of the package. This prevents any adhesive which may emerge at the edge of the patch, during normal storage and transport of the package, from sticking the patch to the package.

Desirably, the patch and release liner can move freely as a unit both in the lateral direction (i.e. in the plane of the patch) and in the vertical direction (i.e. perpendicular to the plane of the patch) within the package.

The border region of the release liner preferably extends continuously around the patch, but the edge of the patch may coincide with the edge of the release liner at one or more zones, provided that the condition is met that the edge of the patch cannot contact the package.

The present invention also provides a kit of parts for use in making such a package.

Preferably the package comprises a container closed by a closure, the container having a central portion at a first depth from the closure joined to an outer portion at a second depth from the closure deeper than the first depth, the outer portion being provided with an outer wall to which the closure is attached, the dimensions being such that with the patch supported on the central portion with the release liner uppermost towards the closure, the edge of the patch lies above said deeper outer portion.

In one preferred form, the patch is mounted on a release liner larger in area than the patch so that the periphery of the patch is spaced inwardly from the periphery of the release liner and the package comprises a container in the form of a moulded sheet and a closure sheet, the container having a flange region surrounding a recess containing the patch and release liner, the recess having a base which includes at least one raised portion located in the base so that, with the patch facing towards the base, the periphery of the patch is maintained spaced from the base in any position of the release liner within the recess, the closure sheet being secured to the flange region.

Preferably the raised portion or portions are spaced from the periphery of the recess, and may take the form of a single raised central region smaller than the patch, or a plurality of raised regions, such as ribs, dispersed over a central area smaller than the patch.

The invention is particularly suitable for a package containing a single patch, but may also for example be used for a package containing a plurality of patches mounted on a single release liner.

DESCRIPTION OF SPECIFIC EMBODIMENT

An embodiment of the invention will now be described by way of example with reference to the following drawings in which:

FIG. 1 is a perspective view from underneath of a package containing a patch which is an embodiment of the invention;

FIG. 2 is an underneath plan view of the package of FIG. 1;

FIG. 3 is a partially cut-away top plan view of the package of FIG. 1;

FIG. 4 is an exploded side view of the package of FIG. 1; and

FIG. 5 is a section along X—X in FIG. 1.

Referring to FIGS. 1–3, a self-adhesive transdermal patch 1 consists of a backing and a thin adhesive layer (not separately shown) of viscous liquid containing an active component, such as a pharmaceutical, to be transported across the skin. This patch 1 is releasably mounted on a release liner 3 by the adhesive layer, with the adhesive layer interposed between the backing and the liner 3. The release liner 3, which may be e.g. a metallized plastics sheet, is larger than the patch 1 which is mounted on a central patch-carrying portion of one surface 6 of the release liner 3 surrounded all around by a border 7. The whole length of the peripheral edge of the patch 1 is inwardly spaced from the edge of the release liner 3. The border 7 is sufficiently wide to facilitate removal of the patch 1 from the release liner 3 by the user and to retain any adhesive escaping from under the patch on the surface 6 substantially to prevent adhesive reaching the edge of the release liner 3.

The release liner 3 is divided into two parts about two-thirds along its length by a slit 9 across its entire width, the two parts being held together by the patch 1. To remove the patch 1 from the release liner 3, the patch 1 is folded back on itself at the slit 9 and a first (e.g. smaller) part of the release liner 3 may be removed. The thus exposed drug-in-adhesive layer of the patch 1 may be applied to the intended site of application on the skin and the second part of the release liner 3 removed, application of the patch 1 being completed by applying pressure to the backing of the patch 1. Thus, in this way, the patch 1 may be applied without any handling of the adhesive surface.

In this specific embodiment, the patch 1 is substantially rectangular, with rounded corners, about 5 cm wide by 6 cm long and the border 7 is uniformly approximately 4 mm wide all around the patch 1, with the slit in the release liner 3 about 22 mm from a short side. Of course a variety of shapes and sizes of patch 1 and release liner 3 may be used depending on the particular application.

The patch 1 mounted on the release liner 3 is stored in a package 10 comprising a container 12 to which a closure 14 is adhesively sealed. In this embodiment the interior of the package 10 is hermetically sealed by the seal of the closure 14, and may be filled with an inert gas, such as nitrogen. The gas pressure helps to prevent the package 10 being compressed. The package 10 is sufficiently rigid to retain its shape and resist deformation under pressures and loads normally encountered in transport and storage. In this embodiment the container is made of transparent moulded plastics material sheet, and the closure 14 is flat, made from flexible metal (aluminium) foil, the package being constructed in the manner of a so-called blister pack with a recess containing the patch and release liner.

As can best be seen from FIGS. 4 and 5, the closure 14 and container 12 can be separated simply by peeling them apart, starting at a tab portion 16 where they are not sealed together. Other typical examples of alternative flexible materials which may provide a peelable closure are plastics sheet, or a laminate comprising aluminium and/or plastics material and/or paper, the closure in this case being flexible and sealed by a suitable adhesive or heat-sealable layer. However, as will be understood, a variety of materials may be used depending on the degree of rigidity or opacity required; for example the container 12 may be made of metal. Opacity may be desirable, to exclude light.

The container 12 has a substantially flat horizontal central portion 18 typically occupying a major part of the area of the container 12. This is joined by a first wall 20 to a surrounding outer portion 22 of greater depth from the closure 14. The outer portion 22 is closed by an outer wall 24, the top of which joins a flange 26 to which the closure 14 is sealed. The tab portion 16 described above is at a part of the flange 26. In this embodiment, the top regions of the first, inner, wall 20, and the outer wall 24 are substantially vertical to provide clearly defined boundaries to the outer portion 22, whereas the bottoms of the first, inner, wall 20 and outer wall 24 curve smoothly to form the bottom 28 of the outer portion 22. With this construction, the outer portion 22 together with the inner and outer walls 20,24 serve to increase the overall rigidity of the package 10. Increased rigidity is provided by a shallow upstand 28a in the outer portion 22.

When the package is in its normal rest position with the closure sheet 14 upwards, the centre of the patch 1 rests on the platform provided by the central portion 18, with the release liner 3 uppermost towards the closure 14. The border 7, described above, prevents the edge of the patch 1 itself contacting the outer wall 24. The central portion 18 is smaller than the patch 1 so that the whole length of the edge of the patch must lie above the trough formed by the outer portion 22.

The depth of the central portion 18 from the closure 14 is greater than the combined thickness of the patch 1 and release liner 3 by an amount sufficient to allow the patch and liner to move freely between contact with the closure 14 and contact with the central portion 18, thus preventing the patch 1 being pinched or compressed between the closure 14 and the central portion 18 in normal conditions, thereby reducing the tendency for the adhesive to be squeezed out from under the patch 1. In particular, the package should withstand the weight of several (e.g. at least a dozen) such packages to enable stacking for transport. Typical pressures which the container should withstand without the patch being compressed are 100 grams spread over 1 square centimeter, and 200 grams spread over the entire patch.

The depth of the outer portion 22 from the closure 14 is greater than that of the central portion 18 by an amount sufficient to prevent the edges 1a,1b of the patch 1, or adhesive escaping outwardly therefrom, contacting the bottom 28.

In this embodiment, the central portion 18 is about 2.5 mm deep from the closure 14 and the outer portion 22 is about 6.5 mm deep from the closure 14 so the difference is about 4 mm. If the release liner 3 and package 10 are sufficiently rigid, the difference in depths and/or the overall depth may be reduced without the edges 1a,1b of the patch contacting the bottom 28.

As can be seen from the section shown in FIG. 5, the sum of the width a of the outer portion 22a at a first side and the width b of the central portion 18 is less than the sum of the width c of the border 7a of the release liner at the first side and the width d of the patch 1. Thus the edge 1b of the patch 1, where adhesive may escape, is made to remain within the second outer portion 22b of the container, away from the inner wall portion 20b, by the edge of the first border portion 7a abutting the first outer wall portion 24a or by the edge of the opposite border portion 7b contacting the wall portion 24b. This is true for any cross-section, and for all locations and orientations to which the patch 1 can move within the package 10, so that no part of the peripheral edge of the patch 1 can contact the inner wall 20.

In this embodiment, with a patch of the dimensions given above, the container 12 has a central portion 18 38 mm wide, bordered by the outer portion 22 which is 13 mm wide to give a total overall width of 64 mm. The central portions 44 mm long, bordered by outer portion 22 which is 15 mm long to give an overall length of 74 mm. The bottom 28 of the outer portion 22 curves smoothly into the inner wall 20 and outer wall 24 via arcuate sections respectively having radii of curvature of approximately 4 mm. The same package 10 can accommodate alternative sizes and shapes of patches if desired, provided the edges of the patch are prevented from contacting the walls of the package as described above.

As described above, the inner and outer walls 20,24 in this embodiment are smooth and continuous, and the boundaries of the outer portion 22 are clearly defined. However, as will be appreciated, the outer wall 24 (for example) may be interrupted by ribs or the like which obstruct movement of the release liner, the central portion 18 need not be flat, and the transition between the central portion 18 and the outer portion 22 need not be so abrupt. The central portion 18 may be a continuous upstanding rib or a plurality of upstanding areas. The important requirement in these embodiments is that the central portion supports the patch, preferably over a major part of the area of the patch, so that the edges of the patch cannot contact the central portion, or other parts of the container. The width a of the outer portion is then measured from a point (e.g. a rib) 24*a* (corresponding to the outer wall 24) which obstructs movement of the release liner 3 to the first point 20*a* where the depth is such that the central portion can contact the patch 1, and the effective width b of the central portion is measured therefrom to the furthest point 20*b* at which the depth is such that the central portion 18 can contact the patch 1. In all cases, the effective width b of the central portion 18 along any given section is less than the corresponding width d of the patch 1.

Furthermore, if, as in the above described embodiment, the release liner 3 is not circular, the dimensions of the package 10 are usually chosen so that the release liner 3 cannot rotate within the package 10; the central portion 18 should be unable to contact the edges 1*a*,1*b* of the patch 1 in any location or orientation of the patch 1 possible within the package 10.

The invention is applicable to the packaging of medical, veterinary and non-medical and non-veterinary patches for application to human or animal skin.

I claim:

1. A package containing a patch for application to the skin, the patch including a backing sheet, an adhesive layer, on said backing sheet, having a first surface and a second surface, and a release liner sized larger than said backing sheet and attached to said second surface of said adhesive layer, the packaging comprising:

a container, of molded material, having a predetermined shape defining a recess sized to contain said patch, said recess being defined by a base wall and a peripheral wall upstanding from said base wall;

a flexible closure sealed to said container so as to cover over said recess;

said base wall of said recess having a first, outer, peripheral region adjacent said peripheral wall, and having a second region surrounded, by said outer peripheral region and being at least partly raised relative to said outer peripheral region so as to provide for said patch a support surface closer to said closure than to said outer peripheral region;

said patch being disposed in said package with said backing sheet lying against said support surface;

each of said recess, said second region of said base wall, said release liner, and said backing sheet sized such that in all positions of said patch within said package, a peripheral edge of said backing sheet lies above and spaced from said outer peripheral region of said base wall and does not contact said support surface;

said closure and said support surface being spaced apart by a distance substantially greater than a total thickness of said patch whereby said patch is prevented from being compressed between said closure and said support surface when said container retains its said predetermined shape and adhesive from said patch is prevented from contact with said package.

2. A package according to claim 1 wherein:

said container is filled with inert gas.

3. A package according to claim 1, wherein said container is hermetically sealed to said closure.

4. A package according to claim 1, wherein said container is fabricated from a plastic material.

5. A package according to claim 1, wherein said closure is fabricated from a metal foil material.

6. A package according to claim 1, wherein said adhesive layer includes a pharmaceutical agent.

7. A package according to claim 1, wherein said adhesive layer includes a beneficial agent.

8. A package according to claim 1, wherein said patch is a medicated transdermal patch.

* * * * *